United States Patent
Dokunikhin et al.

[11] 3,959,285
[45] May 25, 1976

[54] IMIDES OF 1,1'-DINAPHTHYL-4,4',5,5',8,8'-HEXACARBOXYLIC ACID

[76] Inventors: Nikolai Stepanovich Dokunikhin, Presnensky val, 42, kv. 23; Georgy Nikolaevich Vorozhtsov, Sadovaya-Spasskaya ulitsa, 21, kv. 268, both of Moscow, U.S.S.R.

[22] Filed: Apr. 24, 1972

[21] Appl. No.: 246,521

[30] Foreign Application Priority Data
Apr. 28, 1971 U.S.S.R. ............................ 1646220

[52] U.S. Cl. .................. 260/281 NH; 260/251 A; 260/282; 260/281 P; 8/54.2; 8/62
[51] Int. Cl.² ........................................ C07D 217/24
[58] Field of Search .................................. 260/281

[56] References Cited
UNITED STATES PATENTS
2,409,851  10/1946  Haddoch ........................... 260/281
FOREIGN PATENTS OR APPLICATIONS
1,445,775  3/1969  Germany

*Primary Examiner*—Raymond V. Rush
*Assistant Examiner*—Mark L. Berch
*Attorney, Agent, or Firm*—Holman & Stern

[57] ABSTRACT
Novel dinaphthyl derivatives characterized by the general formula

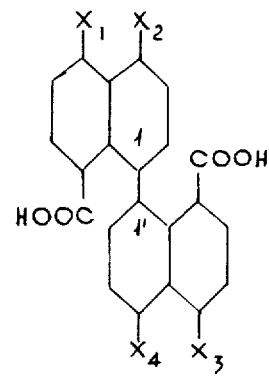

where $X_1$, $X_2$, and $X_3$, $X_4$ represent a group O=C—Y—C=O, wherein Y is an imino group, either unsubstituted or containing one of the following substituents: alkyl, cycloalkyl, aryl, and neterocycle, either unsubstituted or containing one of the following substituents: amino group, halogen, alkoxy, alkyl; or one X of the pair $X_1$, $X_2$; and one X of the pair $X_3$, $X_4$ represent a group —C=O and then the other X is in the benzimidazole or perinone cycle, the compounds of said formula being either symmetrical or non-symmetrical with respect to the 1,1'-bond.

Said derivatives are produced by reacting 1,1'-dinaphthyl-4,4',5,5',8,8' hexacarboxylic acid with a compound of the general formula R-NH₂, where R is hydrogen, alkyl, cycloalkyl, aryl, or heterocycle, either unsubstituted or containing one of the substituents: amino group, halogen, alkoxy, alkyl, in a solvent or in excess compound of the formula R-NH₂.

Said derivatives are employed for producing perylenetetracarboxylic acid derivatives either in their free form or directly on a textile material in the process of dyeing or textile printing.

8 Claims, No Drawings

IMIDES OF 1,1'-DINAPHTHYL-4,4',5,5',8,8'-HEXACARBOXYLIC ACID

The present invention relates to a method of producing dinaphthyl derivatives which may find applications as starting products for the synthesis of pigments and dyes, such as derivatives of perylenetetracarboxylic acid.

Perylenetetracarboxylic acid is known to be produced under rather drastic conditions by alkaline melting of naphthalimide at a temperature of 280° to 300°C, followed by treatment with sulphuric acid (cf. German Pat. Nos. 276,357; 394,794). Derivatives of perylenetetracarboxylic acid produced by condensation of perylenetetracarboxylic acid with amines (cf. German Pat. No. 386,057; FRG Pat Nos. 1,132,272; 1,130,099; 1,138,876) find application as vat dyes and pigments (Colour Index, Soc. Dyers and Colourists, 1956, vol. 3, No. 71130, 71135, 71140).

However, wide application of these compounds as vat dyes is limited due to a low solubility of their reduced form. Some derivatives of perylenetetracarboxylic acid, such as products of condensation of perylenetetracarboxylic acid with ortho-phenylenediamine, have found no application at all, since they give dull blue hues which change under the effect of water drops.

It is an object of the present invention to provide novel dinaphthyl derivatives suitable for producing dyes and pigments.

Another object of the invention is to provide a method of producing dinaphthyl derivatives.

Yet another object of the invention is to provide a new method for the synthesis of perylenetetracarboxylic acid derivatives under less drastic conditions.

The instant invention proposes dinaphthyl derivatives of the general formula (I)

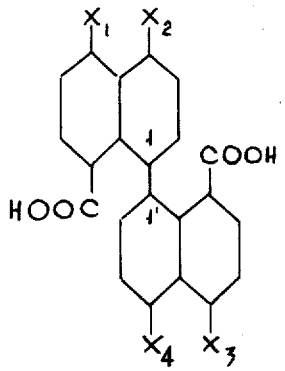

where $X_1$, $X_2$ and $X_3$, $X_4$ represent a group O=λC—Y—C=O, wherein Y is an imino group, either unsubstituted or containing one of the substituents: alkyl, cycloalkyl, aryl, or heterocycle, either unsubstituted or containing one of the substituents: amines, halogen, alkoxy, alkyl; or one X of the pair $X_1$, $X_2$ and one X of the pair $X_3$, $X_4$ represent a group —C=O and then the other X is, respectively, in the benzimidazole or perinone cycle; the compounds of the general formula (I) may be either symmetrical or non-symmetrical with respect to the 1,1'-bond.

Said compounds are novel and have not been described in the literature. They are powders with a high melting point (mainly above 300°C), scarcely soluble in water, and, when reacted with basic agents, give water-soluble salts.

In accordance with the invention, compounds of the general formula (I) are produced by the condensation of 1,1'-dinaphthyl-4,4',5,5',8,8'-hexacarboxylic acid or its anhydride with compounds of the general formula R-NH$_2$ where R is hydrogen, cycloalkyl, aryl, or heterocycle, either unsubstituted or containing substituents such as amino group, halogen, alkyl, alkoxy.

The condensation may be carried out in various solvents which do not interact with the starting reagents and do not interfere with the course of the main reaction. The choice of the solvent is determined by the nature of the amine employed. Water, ethanol, dimethyl or diethylaniline, xylenes and halogen derivatives of benzene can be used as such solvents.

The reaction of condensation can be carried out in excess compound of the general formula R-NH$_2$. The resulting compounds of the general formula (I) are separated by conventional methods, e.g., by filtration.

The condensation reaction can be conducted in the presence of condensating agents having acidic character, such as acetic acid.

For converting the compounds of the general formula (I) into perylenetetracarboxylic acid derivatives of the general formula (II)

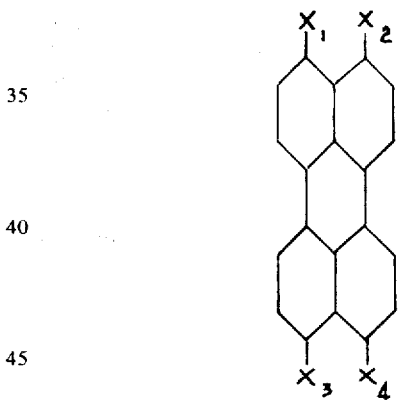

where $X_1$, $X_2$, $X_3$, $X_4$ are as defined above, the compounds having the general formula (I) are treated with a reducing agent in an alkaline medium, this being followed by oxidation. As reducing agents use may be made of various reducing agents, such as those employed in dyeing with vat dyes (hydrosulphite, Rongalite, etc.). As oxidants use may be made of atmospheric oxygen, solutions of hydrogen peroxide, Na$_2$Cr$_2$O$_7$ or K$_2$Cr$_2$O$_7$, etc. The reaction of cyclization proceeds under mild conditions and therefore the above-said dinaphthyl derivatives can find wide application.

The compounds of the general formula (II) can be either isolated in their free form by conventional methods or formed directly on the fibre.

According to the invention, dyeing of textile materials is performed by treating them with an alkaline solution of compounds of the general formula (I) in the presence of reducing agents, followed by oxidation. This results in the formation of perylenetetracarboxylic acid derivatives on the fibre.

According to the invention, printing on textile materials is performed by preparing a printing paste, comprising a compound of the general formula (I), glycerine, a starch-tragacanth thickener, Rongalite, potassium carbonate and water, applying said paste onto the fabric, with subsequent oxidation and washing thereof. In the areas of the paste application a compound of the formula (II) is formed on the textile material.

The dyeing and printing of textile materials with mixtures of the compounds of the formula (I) gives colours ranging from red to blue.

The resulting colours are noted for their high colouristic characteristics.

Salts of the compounds of formula (I) being soluble in water, their practical application for dyeing textile materials becomes substantially simplified. Contrary to the case of usual vat dyes it is no longer necessary to prepare delivery forms of dyes, and the stage of their preliminary reduction is obviated. In case of dibenzimidazoles corresonding to the perylenetetracarboxylic acid derivatives synthesized by the present method, the resultant blue and blue-violet colours are noted for pure tint and do not change under the effect of water drops.

For a better understanding of the present invention, the following illustrative examples are given hereinbelow.

EXAMPLE 1 a. To a suspension of 10.0 g of 1,1'dinaphthyl-4,4'-5,5',8,8'-hexacarboxylic acid anhydride in 90 ml of glacial acetic acid 6.0 ml of aniline are added and the mixture is boiled for 4 hours. The reaction mass darkens and a crystalline precipitate falls out. The reaction mass is allowed to cool down and then is poured onto a triple amount of water, after which it is filtered off, washed with water and dried. 11.0 g of N,N'-diphenyldiimide of 1,1'-dinaphthyl-4,4',5,5',8,8'-hexacarboxylic acid are obtained in the form of bright-yellow prisms (from acetic acid). The compound does not melt till 300°C.

By a similar procedure, from 1,1'-dinaphthyl-4,4',5,5',8,8'-hexacarboxylic acid anhydride and aniline in paraxylene the same N,N'-diphenyldiimide of 1,1'-dinaphthyl-4,4',5,5',8,8'-hexacarboxylic acid is produced.

Found, %: N, 4.30; 4.55. $C_{38}H_{20}N_2O_8$.

Calculated, %: N, 4.43.

b. 20.0 g of 1,1'-dinaphthyl-4,4',5,5',8,8'-hexacarboxylic acid in 60 ml of aniline whereto 5 drops of glacial acid are ddded are heated at a temperature of 180°C for 2 hours. The reaction mass is allowed to cool, and then the precipitate is filtered off, washed with a small quantity of aniline, then with benzene, with alcohol, and dried. 16.7 g of N,N'-diphenyldiimide of 1,1'-dinaphthyl-4,4',5,5',8,8'-hexacarboxylic acid are obtained.

By a similar procedure, from 1,1'-dinaphthyl-4,4',5-,5',8,8'-hexacarboxylic acid and anailine in diethylaniline, dimethylaniline or trichlorobenzene N,N'-diphenyldiimide of 1,1'-dinaphthyl-4,4',5,5',8,8'-hexacarboxylic acid is produced.

c. 10.0 g of 1,1'-dinaphthyl-4,4',5,5',8,8'-hexacarboxylic acid and 7 ml of aniline are boiled in 300 ml of water for 4 hours. Upon cooling, the precipitate is filtered off, washed with water and dried, 8.0 g of N,N'-diphenyldiimide of 1,1'-dinaphthyl-4,4',5,5',8,8'-hexacarboxylic acid are obtained.

The identity of the products obtained in (a), (b) and (c) is confirmed by the coincidence of their IR-spectra.

By adding to the aqueous paste of N,N-diphenyldiimide of 1,1'-dinaphthyl-4,4',5,5',8,8'-hexacarboxylic acid equivalent quantities of KOH, NaOH, $Na_2CO_3$, $K_2CO_3$, $NH_4OH$ and triethanolamine corresponding water-soluble salts are produced:

sodium salt — a light-green product;
ammonium salt — a light-green product;
salt with triethanolamine — a yellow-green product.

Production of N,N'—diphenyldiimide of perylenetetracarboxylic acid d. 0.6 g of N,N-diphenyldiimide of 1,1'-dinaphthyl-4,4',5,5',8,8'-hexacarboxylic acid (or its salt) are dissolved in 100 ml of 2% NaOH solution, 1.5 g of hydrosulphite are added thereto, and the mixture is heated to a temperature of 80° to 85°C. Then the mixture is kept at this temperature for 30 min. During the keeping, the alkali and hydrosulphite must be in excess. After the keeping, air is blown through the reaction mass. The resulting precipitate is filtered off, washed with water and dried. 0.45 g of N,N'-diphenyldiimide of perylenetetracarboxylic acid are obtained, the product being of bright-red colour. The IR-spectrum of the product thus obtained coincides with that of the product prepared by condensation of perylenetetracarboxylic acid anhydride with aniline.

e. A 5 g specimen of a cotton fabric is immersed into a solution containing of 0.2 g of N,N'-diphenyldiimide of 1,1'-dinaphthyl-4,4',5,5',8,8'-hexacarboxylic acid, 1.0 g of NaOH and 1.0 g of hydrosulphite in 200 ml of water. The solution is heated to 80°C and kept for 1 hour. Then the fabric specimen is washed with cold water with an addition of a small quantity of hydrogen peroxide till bright-red, N,N-diphenyldiimide of perylenetetracarboxylic acid is formed on the fabric.

f. A mixture consisting of 1.0 g of N,N'-diphenyldiimide of 1,1'-dinaphthyl-4,4',5,5',8,8'-hexacarboxylic acid, 4 g of glycerine, 30 g of a starch-tragacanth thickener, 5 g of sodium carbonate, 5 g of Rongalite and 5 ml of water is applied onto a cotton fabric and kept at a temperature of 100° to 105°C for a period of 5 to 10 minutes. Then the specimen is thoroughly washed with water, immersed into a solution containing 1 g/l of $Na_2Cr_2O_7$ and 1–2 g/l of acetic acid, and washed with water.

In those places where the mixture was applied onto the fabric bright-red N,N'-diphenyldiimine of perylenetetracarboxylic acid is formed.

EXAMPLE 2 a. To a suspension of 30.0 g of 1,1'-dinaphthyl-4,4',5,5',8,8'-hexacarboxylic acid in 350 ml of glacial acetic acid there are added 23.3 g of para-anisidine and the mixture is boiled for 3 hours. After the cooling, the resulting precipitate is filtered off, washed with acetic acid and dried. 34.5 g of N,N'-di-(p-methoxyphenyl)-diimide of 1,1'-dinaphthyl-4,4',5,5',8,8'-hexacarboxylic acid are obtained in the form of bright-yellow prisms (from acetic acid); the product does not melt till 300°C.

Found, %: N, 4.00; 3.79. $C_{38}H_{24}N_2O_{10}$.

Calculated, %: N, 4.19.

11.5 g of N,N'-di(p-methoxyphenyl)diimide of 1,1'-dinaphthyl-4,4',5,5',8,8'-hexacarboxylic acid can be additionally isolated from the filtrate by diluting it with water.

The last-mentioned compound can also be produced under the conditions similar to those described in Example 1 (c). From N,N'-di-(p-methoxyphenyl)diimide of 1,1'-dinaphthyl-4,4',5,5',8,8'-hexacarboxylic acid by reacting it with alkaline agents as in Example 1 corresponding salts are produced.

PRODUCTION OF N,N'-DI(P-METHOXYPHENYL)DIIMIDE OF PERYLENETETRACARBOXYLIC ACID b. 0.5 g of N,N'-di(p-methoxyphenyl)diimide of 1,1'-dinaphthyl-4,4',5,5',8,8'-hexacarboxylic acid (or its salt) are dissolved in 100 ml of a 2% NaOH solution, 1.5 g of hydrosulphite are added thereto, and the mixture is heated to a temperature of 80° to 85°C. At this temperature the mixture is kept for 30 min. During the keeping the alkali and hydrosulphite must be in excess. Then the reaction mass is blown with air. The resulting precipitate is filtered off, washed with water and dried. 0.4 g of N,N'-di-(p-methoxyphenyl)diimide of perylenetetracarboxylic acid are obtained. The product is of bright-red colour. The IR-spectrum of the product thus produced coincides with that of the product prepared by condensation of perylenetetracarboxylic acid anhydride with p-anisidine.

c. A 5 g linen fabric specimen is immersed into a solution consisting of 0.2 g of N,N'-di(p-methoxyphenyl)diimide of 1,1'-dinaphthyl-4,4',5,5',8,8'-hexacarboxylic acid, 1.0 g of NaOH and 1.0 g of hydrosulphite in 200 ml of water. The solution is heated to 80°C and kept for one hour. Then the specimen is washed with cold water till bright-red N,N'-di(p-methoxyphenyl)diimide of perylenetetracarboxylic acid is formed thereon.

d. A mixture consisting of 1.0 g of N,N'-di(p-methoxyphenyl)diimide of 1,1'-dinaphthyl-4,4',5,5',8,8'-hexacarboxylic acid, 4 g of glycerine, 30 g of a starch-tragacanth thickener, 5 g of Rongalite 5 g of potassium carbonate and 5 ml of water is applied onto a linen fabric specimen and kept at a temperature of 100° to 105°C for a period of 5 to 10 min. Then the fabric specimen is washed thoroughly with water with addition of a small quantity of hydrogen peroxide. In whose places where the mixture was applied onto the fabric bright-red N,N'-di(p-methoxyphenyl)diimide of perylenetetracarboxylic acid is formed.

EXAMPLE 3 a. To a suspension of 30.0 g of 1,1'-dinaphthyl-4,4',5,5',8,8'-hexacarboxylic acid in 300 ml of glacial acetic acid 18.0 g of p-chloroaniline are added and the mixture is boiled for three hours. After the cooling, the resulting precipitate is filtered off, washed with acetic acid and dried. 21.5 g of a bright-yellow precipitate of N,N'-di(p-chlorophenyl)diimide of 1,1'-dinaphthyl-4,4',5,5',8,8'-hexacarboxylic acid are obtained in the form of bright-yellow prisms (from acetic acid); the product does not melt till 300°C.

Found, %: N, 3.87; 3.44. $C_{38}H_{18}N_2Cl_2O_8$.

Calculated, %: N, 3.99.

b. 1.0 g of 1,1'-dinapthyl-4,4',5,5',8,8'-hexacarboxylic acid and 1.0 g of p-chloroaniline are heated with 30 ml of water in a sealed ampoule at a temperature of 120°C for 2.5 hours. The resulting precipitate is filtered off, washed with water, with alcohol, and dried. 1.1 g of N,N'-di(p-chlorophenyl)diimide of 1,1'-dinaphthyl-4,4',5,5',8,8'-hexacarboxylic acid are obtained. The identity of the product thus obtained with that produced by the procedure described in (a) is confirmed by the coincidence of their respective IR-spectra.

From the thus obtained N,N'-di(p-chlorophenyl)diimide of 1,1'-4,4',5,5',8,8'-hexacarboxylic acid corresponding salts are produced by reacting the compound with alkaline agents of Example 1.

PRODUCTION OF N,N'-DI(P-CHLOROPHENYL)DIIMIDE OF PERYLENETETRACARBOXYLIC ACID c. 0.5 g of N,N'-di(p-chlorophenyl)diimide of 1,1'-dinaphthyl-4,4',5,5',8,8'-hexacarboxylic acid (or its salt) are dissolved in 100 ml of a 2% NaOH solution, 1.5 g of hydrosulphite are added thereto, and the mixture is heated to a temperature of 80° to 85°C. The keeping at this temperature lasts for 30 min. During the period of keeping, the alkali and hydrosulphite must be in excess. Then the reaction mass is blown with air. The resulting precipitate is filtered off, washed with water and dried. 0.4 g of bright-red N,N'-di(p-chlorophenyl)-diimide of perylenetetracarboxylic acid are obtained. The IR-spectrum of the product thus produced coincides with the IR-spectrum of the product prepared by condensation of perylenetetracarboxylic acid anhydride with p-chloroaniline.

d. A 5 g rayon fabric specimen is immersed into a solution consisting of 0.2 g of N,N'-di(p-chlorophenyl)diimide of 1,1'-dinaphthyl-4,4',5,5',8,8'-hexacarboxylic acid, 1.0 g of NaOH and 1.0 g of hydrosulphite in 200 ml of water, the solution is heated to 80°C and kept at this temperature for one hour. Then the fabric specimen is washed with cold water till bright-red N,N'-di(p-chlorophenyl)diimide of perylenetetracarboxylic acid is formed on the specimen.

e. A mixture consisting of 1.0 g of N,N'-di(p-chlorophenyl)diimide of 1,1'-dinaphthyl-4,4',5,5',8,8'-hexacarboxylic acid, 4 g of glycerine, 30 g of a starch-tragacanth 20 thickener, 5 g of potassium carbonate, 5 g of Rongalite and 5 ml of water is applied onto a rayon fabric and kept at a temperature of 100°to 105°C for a period of 5 to 10 min. Then the fabric specimen is thoroughly washed with water, immersed into a solution containing 1 g/l of $K_2Cr_2O_7$ and 1–2 g/l of acetic acid, and washed with water. In the places where the mixture was applied onto the fabric, bright-red N,N'-di(p-chlorophenyl)diimide of perylenetetracarboxylic acid is formed.

EXAMPLE 4 a. To a suspension of 5.0 g of 1,1'-dinaphthyl-4,4',5,5',8,8'-hexacarboxylic acid in 60 ml of glacial acetic acid 4.5 g of 3,4 -dichloroaniline are added and the mixture is boiled for three hours. After cooling, the resulting precipitate is filtered off, washed with acetic acid and dried. 3.4 g of light-gray N,N'-di(dichlorophenyl)diimide of 1,1'-dinaphthyl-4,4',5,5',8,8'-hexacarboxylic acid are obtained. The substance does not melt till 300°C.

Found, %: N, 2.99; 3.42. $C_{38}H_{16}Cl_4O_8$.

Calculated, %: N, 3.64.

N,N'-di(dichlorophenyl)diimide of 1,1'-dinaphthyl-4,4',5,5',8,8'-hexacarboxylic acid can also be produced under the conditions similar to those described in Examples 1 (c) and 3 (b).

From N',N'-di(dichlorophenyl)diimide of 1,1'-dinaphthyl-4,4',5,5',8,8'-hexacarboxylic acid reacted with the alkaline agents of Example 1 corresponding salts are produced.

PRODUCTION OF N,N-DI(DICHLOROPHENYL)DIIMIDE OF PERYLENETETRACARBOXYLIC ACID b. From 0.6 g of N,N-di-(dichlorophenyl)diimide of 1,1'-dinaphthyl-4,4',5,5',8,8'-hexacarboxylic acid (or its salt) under the conditions described in Example 1 (d) 0.45 g of N,N'-di(dichlorophenyl)diimide of perylenetetracarboxylic acid are obtained. The product is of bright-red colour. The IR-spectrum of the product thus obtained coincides with that of the product produced by condensation of perylenetetracarboxylic acid anhxdride with 3,4-dichloroaninine.

c. From 0.2 g of N,N'-di(dichlorophenyl)diimide of 1,1'-dinaphthyl-4,4',5,5',8,8'-hexacarboxylic acid on a 5 g cotton fabric specimen, under the conditions similar to those described in Example 1 (e) bright-red N,N'-di(dichlorophenyl)diimide of perylenetetracarboxylic acid is produced.

d. From 1.0 g of N,N'-di(dichlorophenyl)diimide of 1,1'-dinaphthyl-4,4',5,5',8,8'-tetracarboxylic acid, under the conditions described in Example 1 (f), bright-red N,N'-di(dichlorophenyl)diimide of perylenetetracarboxylic acid is formed on the cotton fabric specimen in those places which were treated with the starting mixture.

EXAMPLE 5 a. To a suspension of 30.0 g of 1,1'-dinaphthyl-4,4',5,5',8,8'-hexacarboxylic acid in 450 ml of water 25 ml of (25% aqueous solution of) methylamine are added and the mixture is heated to boiling point. The boiling is continued for one hour. Upon cooling, the reaction mass is clarified by filtration. The filtrate is acidulated with HCl till acidic reaction for Congo Red, the precipitate is filtered off, washed with dilute hydrochloric acid, then with a small quantity of water and dried. 22.0 g of light-brown N,N'-dimethyldiimide of 1,1'-dinaphthyl-4,4',5,5',8,8'-hexarboxylic acid are obtained. The product does not melt till 300°C.

Found, %: N, 5.24; 5.15. $C_{28}H_{16}N_2O_8$.
Calculated, %: N, 5.51.

By reacting the N,N'-dimethyldiimide of 1,1'-dinaphthyl-4,4',5,5',8,8'-hexacarboxylic acid with the alkaline agents of Example 1 corresponding salts are produced.

Production of N,N'-dimethyldiimide of perylenetetracarboxylic acid.

b. From 0.4 g of N,N'-dimethyldiimine of 1,1'-dinaphthyl-4,4',5,5',8,8'-hexacarboxylic acid (or its salt) under the conditions described in Example 1, 0.3 g of red-coloured N,N'-dimethyldiimide of perylenetetracarboxylic acid are obtained. The IR-spectrum of the product thus obtained coincides with that of the product prepared by condensation of perylenetetracarboxylic acid anhydride with methylamine.

c. From 0.2 g of N,N'-dimethyldiimide of 1,1'-dinaphthyl-4,4',5,5',8,8'-hexacarboxylic acid, under the conditions described in Example 1 (e), on a 5 g cotton specimen red N,N'-dimethyldiimide of perylenetetracarboxylic acid is formed.

d. 1.0 g of N,N'-dimethyldiimide of 1,1'-dinaphthyl-4,4',5,5',8,8'-hexacarboxylic acid under the conditions as set forth in Example 1 (f) red N,N'-dimethyldiimide of perylenetetracarboxylic acid is formed on the cotton fabric specimen in the places where the application was performed.

EXAMPLE 6 a. To a suspension of 30.0 g of 1,1'-dinaphthyl-4,4',5,5',8,8'-hexacarboxylic acid in 350 ml of glacial acetic acid there are added 13.0 g of o-phenylenediamine and the mixture is boiled for 1.5 hours. Upon cooling, the resulting precipitate is filtered off, washed with acetic acid, then with water, and dried. 27.0 g of 1,1'-bisnaphthylenebenzimidazolone-8,8'-dicarboxylic acid are obtained. The substance is of brown colour; does not melt till 300°C.

Found, %: N, 8.76; 8.47. $C_{38}H_{18}N_4O_6$.
Calculated, %: N, 8.94.

b. 10.0 g of 1,1'-dinaphthyl-4,4',5,5',8,8'-hexacarboxylic acid and 4.6 g of orthophenylenediamine are boiled in 600 ml of a reference aqueous solution (1:1) during 5 hours. Upon cooling, the resulting precipitate is washed with water and dried. 8.2 g of 1,1'-bisnaphthylenebenzimidazolone-8,8'-dicarboxylic acid are obtained. The identity of the products obtained in (a) and (b) is confirmed by the coincidence of their respective IR-spectra.

From 1,1'-bisnaphthylenebenzimidazolone-8,8'-dicarboxylic acid reacted with the alkaline agents of Example 1 corresponding salts are produced.

PRODUCTION OF BISBENZIMIDAZOANTHRADIISOQUINOLINEDIONE c. 0.6 g of diimidazole of 1,1'-dinaphthyl-4,4',5,5',8,8'-hexacarboxylic acid (or its salt) are dissolved in 100 ml of a 2% NaOH solution, 1.5 g of hydrosulphite are added thereto, and the mixture is heated to a temperature of 75° to 80°C. At this temperature the mixture is kept for 30 min. During the keeping the alkali and hydrosulphite must be in excess. Then the reaction mass is blown with air. The resulting precipitate is filtered off, washed with water and dried. 0.5 g of dark-blue diimidazole of perylenetetracarboxylic acid are obtained. The IR-spectrum of the product thus obtained is close to the IR-spectrum of the product prepared by condensation of perylenetetracarboxylic acid anhydride with o-phenylenediamine.

d. A 5 g rayon fabric specimen is immersed into a solution consisting of 0.2 g of 1,1'-bisnaphthylenebenzimidazolone-8,8'-dicarboxylic acid, 0.1 g of NaOH and 1.0 g of hydrosulphite in 200 ml of water. The solution with the specimen is heated to a temperature of 75° to 85°C and kept at this temperature for 1 hour. Then the rayon fabric specimen is washed with cold water till diimidazole of perylenetetracarboxylic acid of blue-violet colour is formed on it.

e. A mixture consisting of 1.0 g of 1,1'-bisnaphthylenebenzimidazolone-8,8'-dicarboxylic acid, 4 g of glycerine, 30 g of a starch-tragacanth thickener, 5 g of potassium carbonate, 5 of Rongalite and 5 ml of water is applied onto a rayon fabric and kept at a temperature of 100°-105°C for a period of 5 to 10 min. Then the fabric is thoroughly washed with water. In the places where the mixture was applied blue-violet diimidazole of perylenetetracarboxylic acid is formed on the rayon fabric.

EXAMPLE 7

To a suspension of 10.0 g of 1,1'-dinaphthyl-4,4',5,5',8,8'-hexacarboxylic acid anhydride in 100 ml of glacial acetic acid 10.0 g of 1,8-naphthylenediamine are added and the mixture is boiled for two hours. The resulting red-brown precipitate is filtered off, washed with acetic acid, then with water, and dried. 9.0 g of a corresponding diperinone are obtained. The substance is of red-brown colour and does not melt till 300°C.

Found, %: N, 7.76; 7.82. $C_{48}H_{22}N_4O_6$.

Calculated, %: N, 7.72.

From the diperinone produced from 1,1'-dinaphthyl-4,4',5,5',8,8'-hexacarboxylic acid, by reacting the former with the alkaline agents of Example 1, corresponding salts are obtained.

Under the conditions described in Example 1 (d), from the diperinone prepared from 1,1'-dinaphthyl-4,4',5,5',8,8'-hexacarboxylic acid, a diperinone containing a perylene structure is produced. The product is of black colour.

Under the conditions described in Example 1 (e), 1 (f), from the diperinone prepared from 1,1'-dinapthyl-4,4',5,5',8,8'-hexacarboxylic acid, a diperinone is formed on a cotton fabric specimen, which contains a perylene structure.

EXAMPLE 8

From 1.0 g of 1,1'-dinaphthyl-4,4',5,5',8,8'-hexacarboxylic acid anhydride and 0.8 g of cyclohexylamine, under the conditions described in Example 1 (b), 1.0 g of N,N'-dicyclohexyldiimide of 1,1-dinaphthyl-4,4',5-,5',8,8'-hexacarboxylic acid are produced. The substance is of greenish-brown colour and does not melt till 300°C.

From N,N'-dicyclohexyldiimide of 1,1'-dinaphthyl-4,4',5,5',8,8'-hexacarboxylic acid reacted with the alkaline agents of Example 1 corresponding salts are produced.

Under the conditions described in Example 1 (d), from N,N'-dicyclohexyldiimide of 1,1'-dinaphthyl-4,4',5,5',8,8'-hexacarboxylic acid N,N'-dicyclohexyldiimide of perylenetetracarboxylic acid, a substance of red colour, is produced.

Under the conditions described in Example 1 (e) and (f), from N,N'-dicyclohexyldiimide of 1,1'-dinaphthyl-4,4',5,5',8,8'-hexacarboxylic acid, N,N'-dicyclohexyldiimide is formed on a cotton fabric specimen.

EXAMPLE 9

From 1.0 g of 1,1'-dinaphthyl-4,4',5,5',8,8'-hexacarboxylic acid anhydrid and 1.0 g of 2-aminopyridine under the conditions described in Example 3 (b) 1.0 g of N,N'-dipyridyliimide of 1,1'-dinapthyl-4,4',5,5',8-,8'-dicarboxylic acid are obtained. The substance is of brown colour and does not melt till 300°C.

From N,N'-dipyridyldiimide of 1,1'-dinaphthyl-4,4',5,5',8,8'-hexacarboxylic acid reacted with the alkaline agents of Example 1 corresponding salts are produced.

Under the conditions described in Example 1 (d), from N,N'-dipyridyldiimide of 1,1'-dinapthyl-4,4',5-,5',8,8'-hexacarboxylic acid N,N'-dipyridyldiimide of perylenetetracarboxylic acid, a substance of red colour, is produced.

Under the conditions described in Example 1 (e) and (f), from N,N'-dipyridyldiimide of 1,1'-dinapthyl-4,4',5,5',8,8'-hexacarboxylic acid, N,N'-dipyridyldiimide of perylenetetracarboxylic acid is formed on a cotton fabric specimen.

What is claimed is:

1. Compounds represented by the formula:

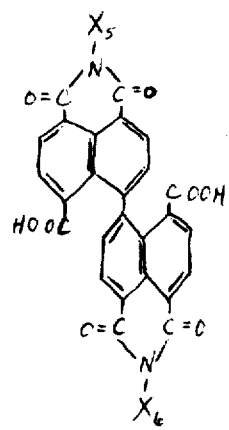

wherein $X_5$ and $X_6$ are the same groups selected from the group consisting of lower alkyl, cyclohexyl, phenyl, lower alkylphenyl, lower alkoxyphenyl, halophenyl and 2-pyridyl.

2. A compound according to claim 1, wherein $X_5$ and $X_6$ are phenyl.

3. A compound according to claim 1, wherein $X_5$ and $X_6$ are p-methoxyphenyl.

4. A compound according to claim 1, wherein $X_5$ and $X_6$ are p-chlorophenyl.

5. A compound according to claim 1, wherein $X_5$ and $X_6$ are dichlorophenyl.

6. A compound according to claim 1, wherein $X_5$ and $X_6$ are methyl.

7. A compound according to claim 1, wherein $X_5$ and $X_6$ are cyclohexyl.

8. A compound according to claim 1, wherein $X_5$ and $X_6$ are 2-pyridyl.

* * * * *